US010219682B2

United States Patent
Hatano (10) Patent No.: US 10,219,682 B2
(45) Date of Patent: Mar. 5, 2019

(54) ENDOSCOPE

(71) Applicant: OLYMPUS CORPORATION, Tokyo (JP)

(72) Inventor: Keisuke Hatano, Koganei (JP)

(73) Assignee: OLYMPUS CORPORATION, Tokyo (JP)

( * ) Notice: Subject to any disclaimer, the term of this patent is extended or adjusted under 35 U.S.C. 154(b) by 3 days.

(21) Appl. No.: 15/597,560

(22) Filed: May 17, 2017

(65) Prior Publication Data

US 2017/0251906 A1    Sep. 7, 2017

Related U.S. Application Data

(63) Continuation of application No. PCT/JP2016/061146, filed on Apr. 5, 2016.

(30) Foreign Application Priority Data

Jun. 29, 2015  (JP) ................................. 2015-130127

(51) Int. Cl.
*A61B 1/005* (2006.01)
*A61B 1/008* (2006.01)
(Continued)

(52) U.S. Cl.
CPC .......... *A61B 1/0057* (2013.01); *A61B 1/0052* (2013.01); *A61B 1/0055* (2013.01);
(Continued)

(58) Field of Classification Search
None
See application file for complete search history.

(56) References Cited

U.S. PATENT DOCUMENTS 4,534,339 A * 8/1985 Collins ................ A61B 1/0052
    600/136
4,552,129 A * 11/1985 Utsugi ............... A61B 1/00137
    600/131
(Continued)

FOREIGN PATENT DOCUMENTS

CN    103222840 A    7/2013
CN    103945754 A    7/2014
(Continued)

OTHER PUBLICATIONS

International Search Report dated Jul. 12, 2016 received in PCT/JP2016/061146.
(Continued)

*Primary Examiner* — Timothy J Neal
*Assistant Examiner* — Jae Woo
(74) *Attorney, Agent, or Firm* — Scully, Scott, Murphy & Presser, P.C.

(57) ABSTRACT

An endoscope includes stays extending inside an operation section along a direction of a longitudinal axis, and a suction pipeline fixed to the operation section at a distal end side and a proximal end side so as to extend inside the operation section, along the stays and in the direction of the longitudinal axis, where an inside of the operation section is partitioned into a first space portion and a second space portion by the stays and the suction pipeline, each angle wire is disposed inside the first space portion, and long internal components, such as a signal cable and a light guide, are disposed inside the second space portion.

2 Claims, 12 Drawing Sheets

(51) Int. Cl.
*A61B 1/015* (2006.01)
*A61B 1/018* (2006.01)

(52) U.S. Cl.
CPC .............. *A61B 1/008* (2013.01); *A61B 1/015* (2013.01); *A61B 1/018* (2013.01)

(56) References Cited

U.S. PATENT DOCUMENTS

| | | | | |
|---|---|---|---|---|
| 4,742,817 A | * | 5/1988 | Kawashima | A61B 1/0052 600/104 |
| 4,841,950 A | * | 6/1989 | Fukuda | A61B 1/0052 600/146 |
| 4,905,666 A | * | 3/1990 | Fukuda | A61B 1/0052 600/146 |
| 4,986,257 A | * | 1/1991 | Chikama | A61B 1/0052 600/146 |
| 5,097,838 A | * | 3/1992 | Hirooka | A61B 1/00098 600/463 |
| 5,098,387 A | * | 3/1992 | Wiest | A61B 1/00068 417/475 |
| 5,167,221 A | * | 12/1992 | Chikama | A61B 1/0052 600/149 |
| 5,301,656 A | * | 4/1994 | Negoro | A61B 1/0052 600/133 |
| 5,312,327 A | * | 5/1994 | Bales | A61B 1/12 604/21 |
| 5,415,158 A | * | 5/1995 | Barthel | A61B 1/00165 600/149 |
| 5,472,017 A | * | 12/1995 | Kovalcheck | A61B 1/0052 138/103 |
| 5,626,553 A | * | 5/1997 | Frassica | A61B 1/0052 600/146 |
| 5,667,476 A | | 9/1997 | Frassica et al. | |
| 6,491,627 B1 | * | 12/2002 | Komi | A61B 1/0052 600/146 |
| 7,785,333 B2 | * | 8/2010 | Miyamoto | A61B 1/00135 600/104 |
| 7,922,650 B2 | * | 4/2011 | McWeeney | A61B 1/00071 600/104 |
| 8,784,299 B2 | * | 7/2014 | Takemoto | A61B 1/0052 600/104 |
| 9,968,241 B2 | * | 5/2018 | Iuel | A61B 1/0052 |
| 2004/0073083 A1 | * | 4/2004 | Ikeda | A61B 1/00039 600/101 |
| 2008/0200763 A1 | * | 8/2008 | Ueno | A61B 1/00039 600/146 |
| 2008/0262293 A1 | * | 10/2008 | Murakami | A61B 1/0052 600/102 |
| 2009/0036742 A1 | * | 2/2009 | Watanabe | A61B 1/00052 600/178 |
| 2010/0217072 A1 | * | 8/2010 | Kondoh | A61B 1/00071 600/101 |
| 2013/0035551 A1 | * | 2/2013 | Yu | A61B 1/0057 600/141 |
| 2014/0165772 A1 | * | 6/2014 | Okazaki | B25J 18/06 74/490.04 |
| 2014/0187864 A1 | | 7/2014 | Kubo | |
| 2015/0025319 A1 | * | 1/2015 | Koyama | A61B 1/0011 600/118 |
| 2017/0065152 A1 | * | 3/2017 | Koyama | A61B 1/00112 |

FOREIGN PATENT DOCUMENTS

| | | |
|---|---|---|
| EP | 1 834 575 A1 | 9/2007 |
| EP | 1 908 390 A1 | 4/2008 |
| JP | H11-192199 A | 7/1991 |
| JP | 8-224211 A | 9/1996 |
| JP | 9-84739 A | 3/1997 |
| JP | H09-164111 A | 6/1997 |
| JP | H10-216078 A | 8/1998 |
| JP | 2000-51148 A | 2/2000 |
| JP | 2012-135515 A | 7/2012 |

OTHER PUBLICATIONS

Extended Supplementary European Search Report dated Jul. 6, 2018 in European Patent Application No. 16 81 7534.7.

* cited by examiner

ENDOSCOPE

CROSS REFERENCE TO RELATED APPLICATION

This application is a continuation application of PCT/JP2016/061146 filed on Apr. 5, 2016 and claims benefit of Japanese Application No. 2015-130127 filed in Japan on Jun. 29, 2015, the entire contents of which are incorporated herein by this reference.

BACKGROUND OF INVENTION

1. Field of the Invention

The present invention relates to an endoscope, a bending portion of which is bent in accordance with operation of an angle wire at an operation section.

2. Description of the Related Art

Conventionally, endoscopes configured to perform various inspections and treatments are widely known in medical and industrial fields. For example, among such endoscopes, medical endoscopes are widely used because the endoscopes are capable of acquiring in-vivo images of an inside of a body cavity without having to cut open a subject, such as a patient, by inserting a flexible elongated insertion section provided with a solid image pickup device at a distal end, and of performing medical treatment as necessary by causing a treatment instrument to protrude from the insertion section distal end.

The insertion section of such an endoscope includes, as internal components, a channel configured to enable insertion of treatment instruments, such as a biological forceps, an electric scalpel and an inspection probe, into the body cavity of a subject, a light guide configured to transmit illumination light, and a signal cable configured to transmit a signal from an image pickup unit provided at the distal end of the insertion section, for example. The internal components extend into an operation section which is continuously provided on a proximal end side of the insertion section.

Furthermore, to increase insertability and observation performance inside a subject, a bending portion is provided continuously to the insertion section of the endoscope, on a proximal end side of a distal end portion. Generally, an angle wire extending from the inside of the operation section to the inside of the insertion section is connected to the bending portion, and the bending portion is bent by pulling or relaxing of the angle wire by a bending knob, a bending lever or the like provided to the operation section (for example, see Japanese Patent Application Laid-Open Publication No. 2012-135515).

SUMMARY OF THE INVENTION

An endoscope according to an aspect of the present invention includes an insertion section configured to be insertable into a subject, and bendable in at least two directions with a longitudinal axis direction as a center, an operation section disposed on a proximal end side of the insertion section, a support member extending inside the operation section, along the longitudinal axis direction, a pipeline section fixed to the operation section at a distal end side and a proximal end side so as to extend inside the operation section, along the support member and in the longitudinal axis direction, and configured to partition, with the support member, an internal space of the operation section into a first space portion and a second space portion, an angle wire disposed in the first space portion inside the operation section, and configured to cause the bending portion to bend, and a long internal component disposed in the second space portion inside the operation section, and extending from the insertion section.

DETAILED DESCRIPTION OF THE PREFERRED EMBODIMENT(S)

Figure 3:
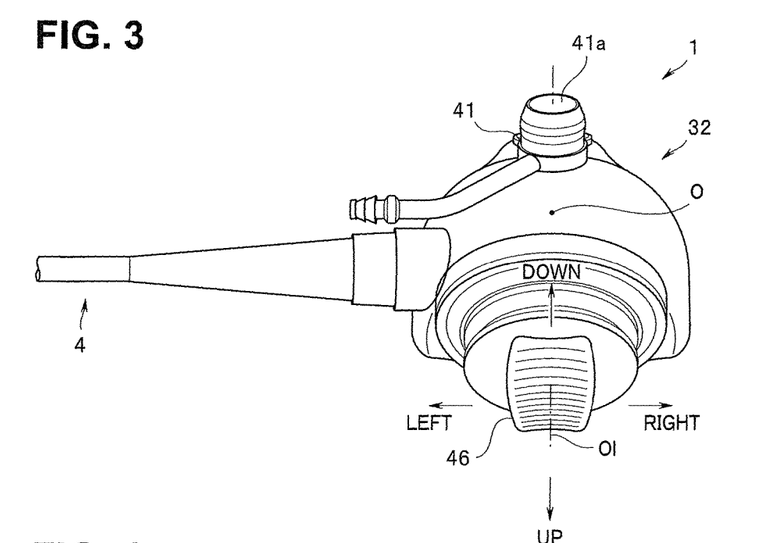
FIG. 3 is a top view showing the external appearance of the endoscope.
Figure 4:
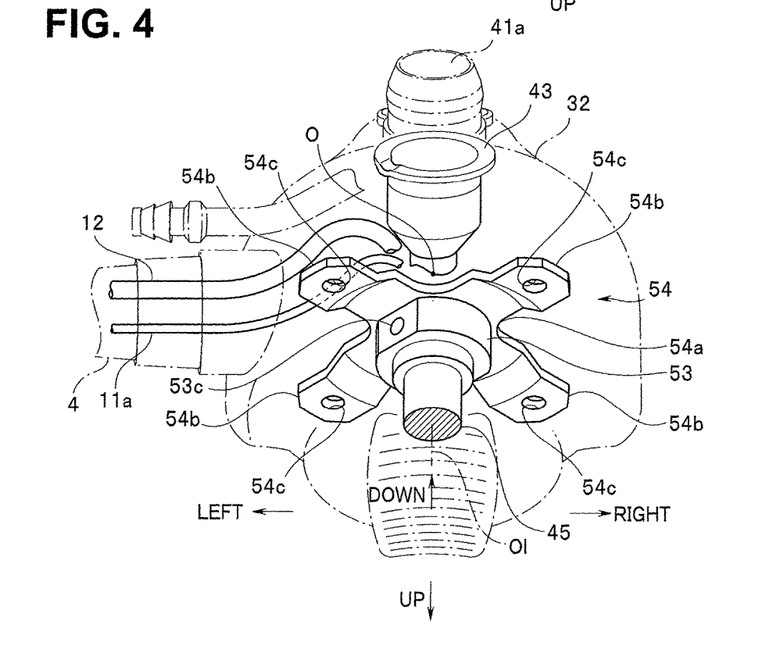
FIG. 4 is an explanatory view showing a positional relationship of a signal cable and a light guide to a wire pull member and a cylinder.
Figure 5:
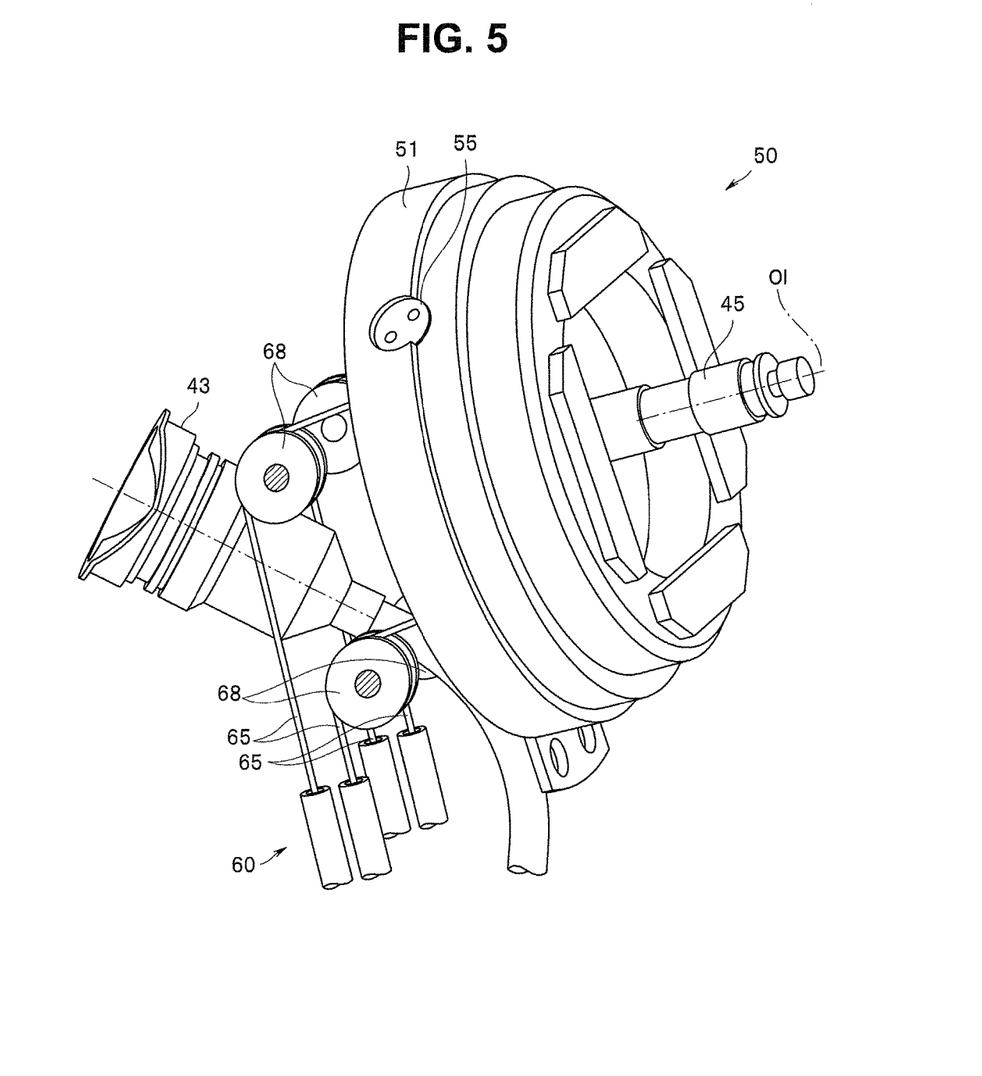
FIG. 5 is a perspective view showing a positional relationship between a wire pull mechanism and the cylinder.
Figure 6:
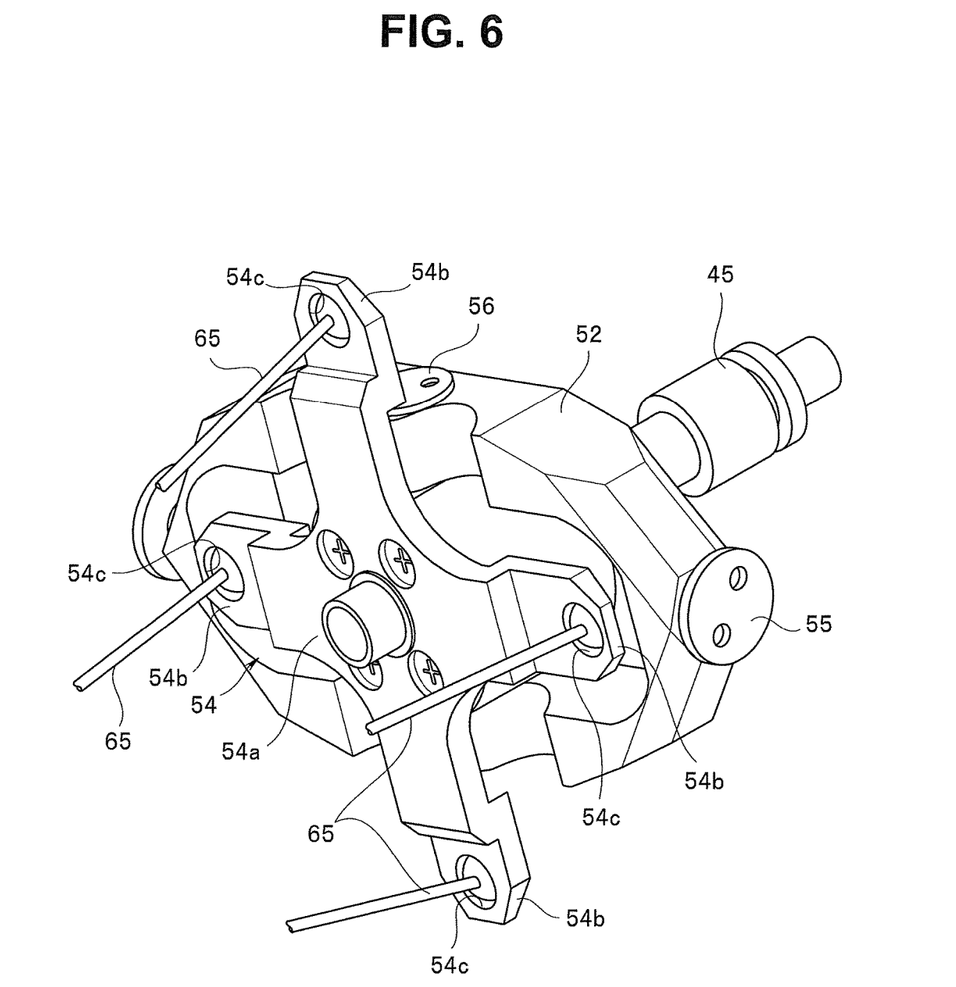
FIG. 6 is a perspective view showing internal structural components of the wire pull mechanism.
Figure 7:
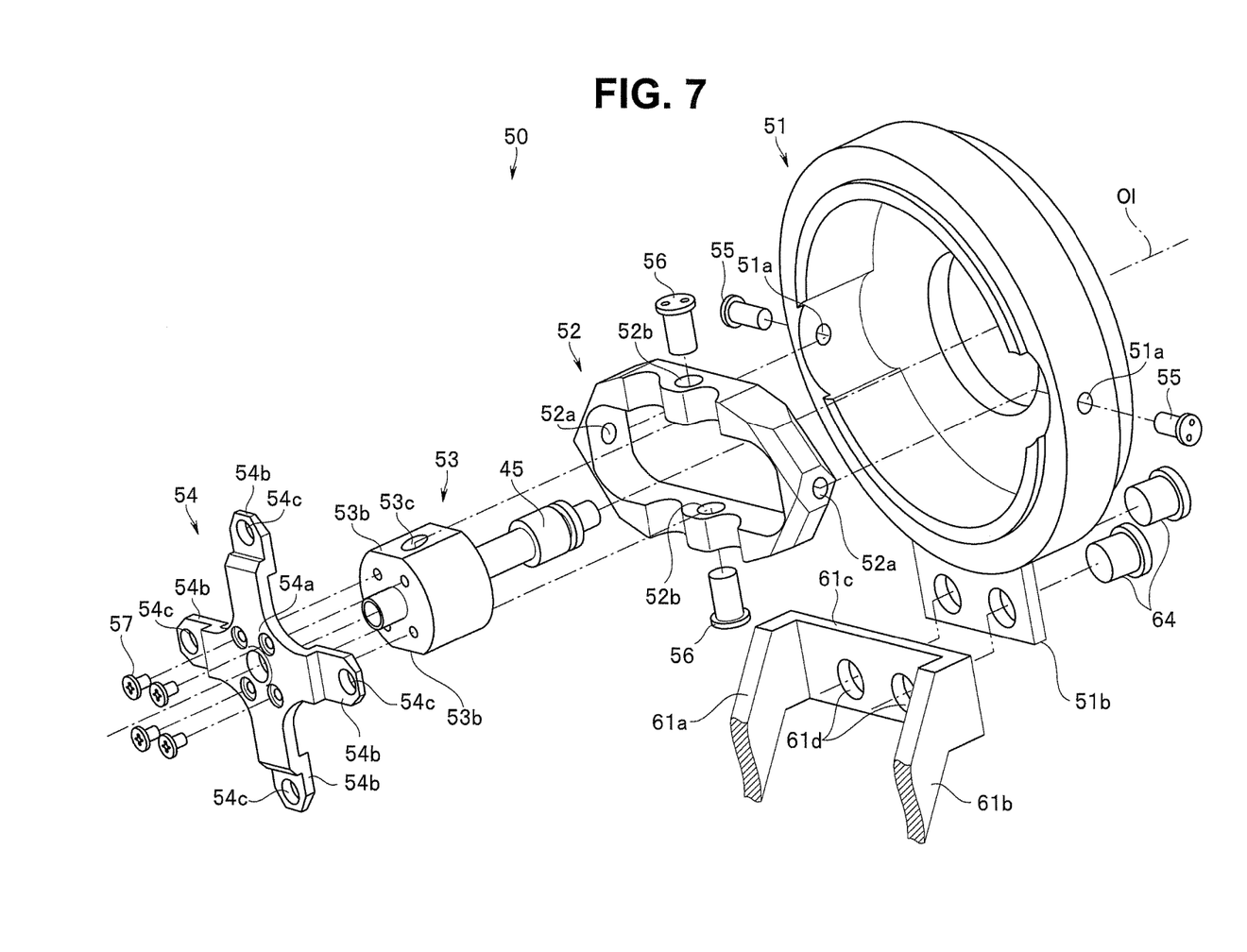
FIG. 7 is an exploded perspective view showing the internal structural components of the wire pull mechanism.
Figure 8:
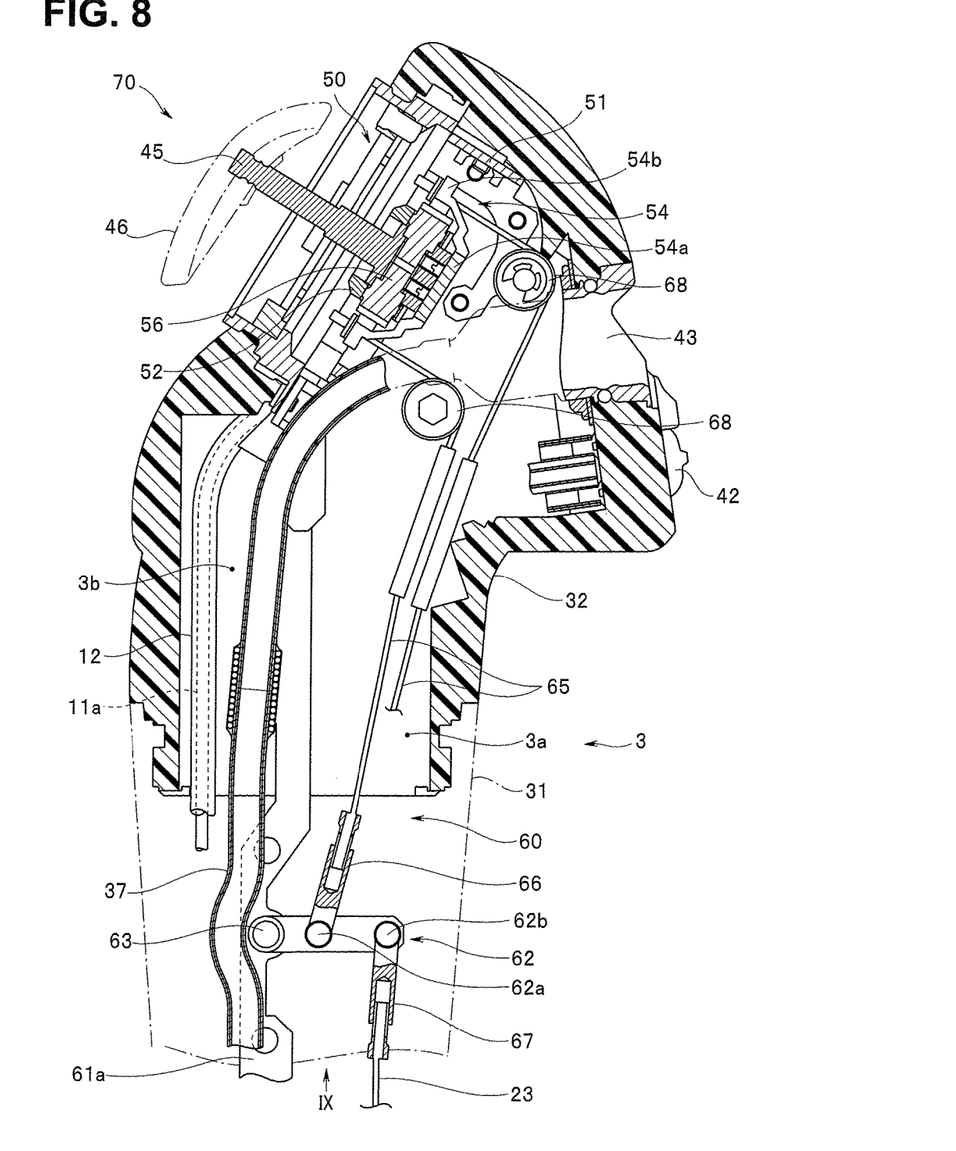
FIG. 8 is a cross-sectional view of main parts of an operation section.
Figure 9:
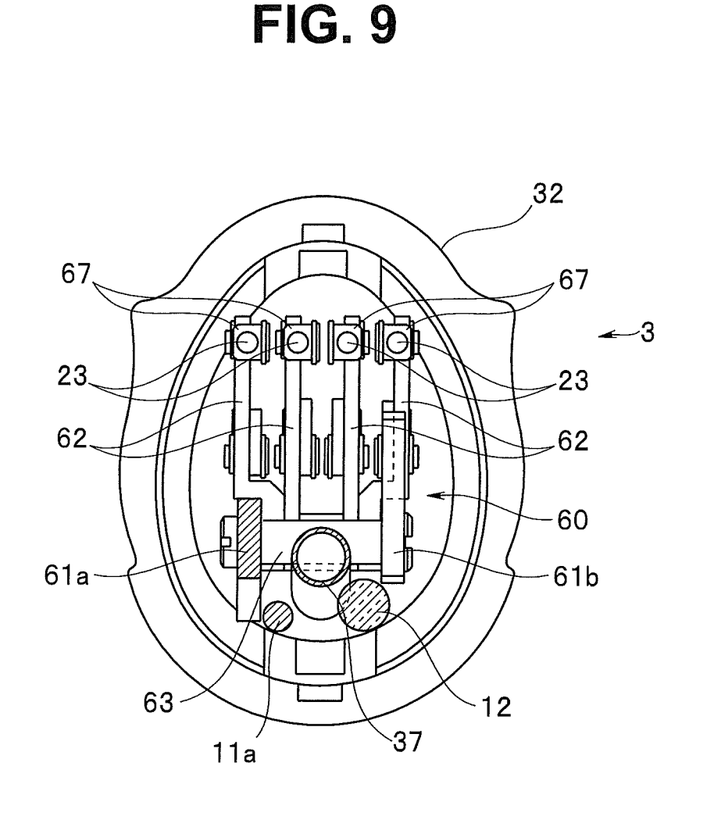
FIG. 9 is a view in the direction of arrow IX in FIG. 8.
Figure 10:
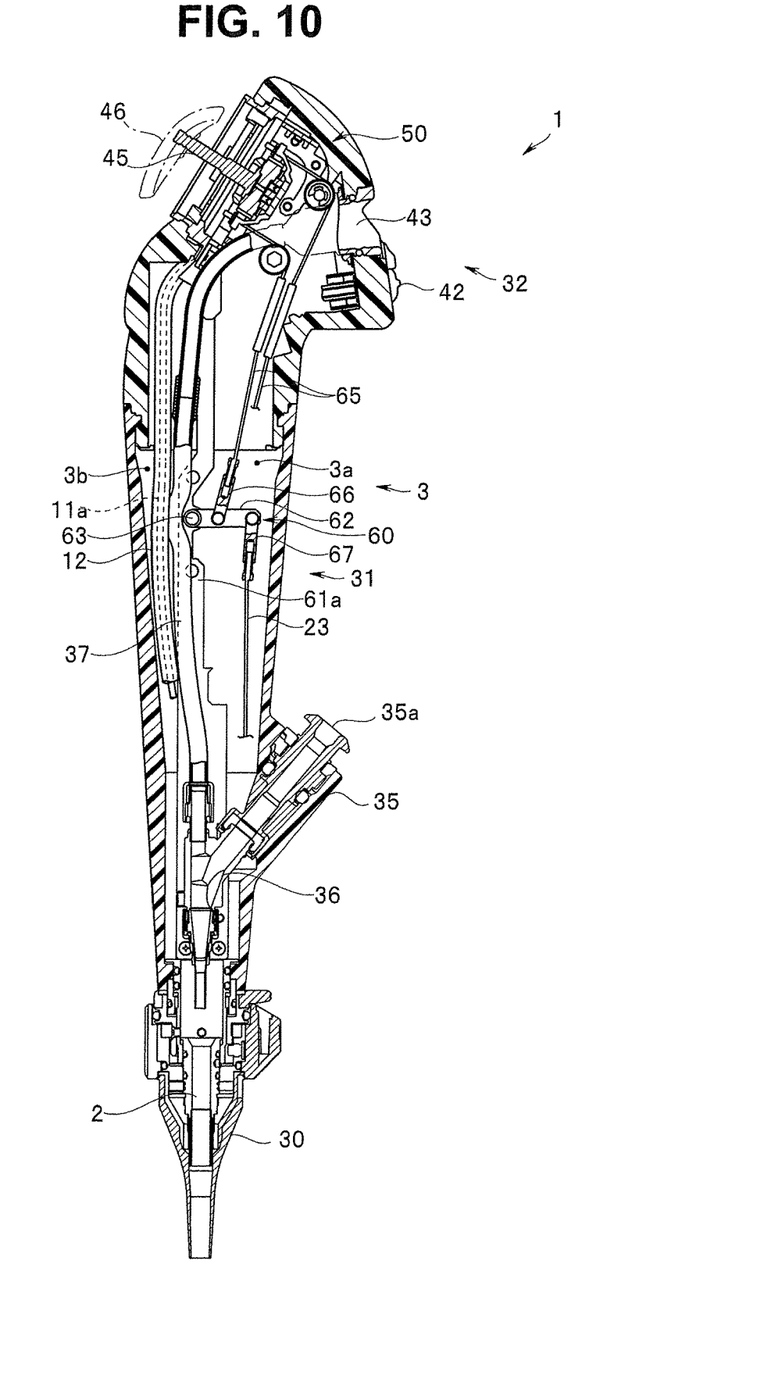
FIG. 10 is a cross-sectional view showing an internal structure of a left-side portion of the operation section.
Figure 11:
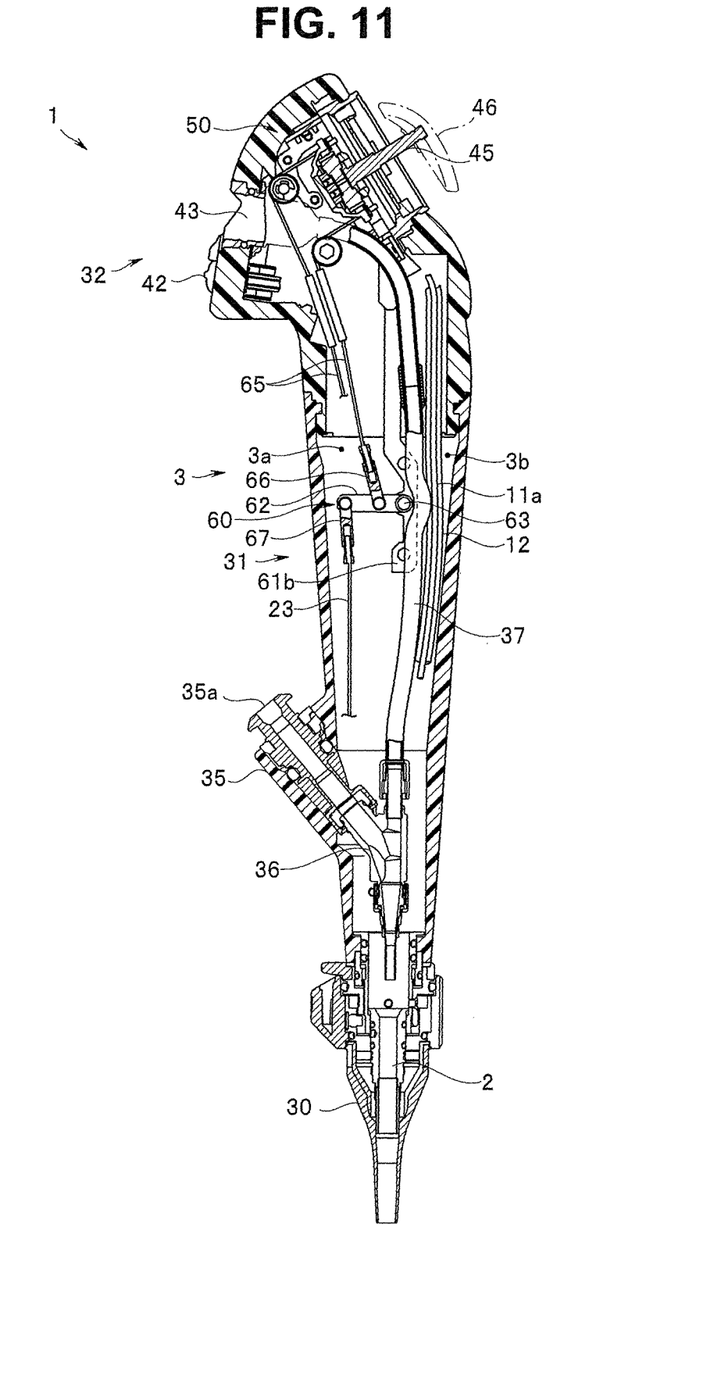
FIG. 11 is a cross-sectional view showing an internal structure of a right-side portion of the operation section.

Hereinafter, a mode of the present invention will be described with reference to the drawings. The drawings relate to an embodiment of the present invention, and FIG. 1 is a front view showing an external appearance of an endoscope, FIG. 2 is a right side view showing the external appearance of the endoscope, FIG. 3 is a top view showing the external appearance of the endoscope, FIG. 4 is an explanatory view showing a positional relationship of a signal cable and a light guide to a wire pull member and a cylinder, FIG. 5 is a perspective view showing a positional relationship between a wire pull mechanism and the cylinder, FIG. 6 is a perspective view showing internal structural components of the wire pull mechanism, FIG. 7 is an exploded perspective view showing the internal structural components of the wire pull mechanism, FIG. 8 is a cross-sectional view of main parts of an operation section, FIG. 9 is a view in the direction of arrow IX in FIG. 8, FIG. 10 is a cross-sectional view showing an internal structure of a left-side portion of the operation section, FIG. 11 is a cross-sectional view showing an internal structure of a right-side portion of the operation section, FIG. 12 is a transverse cross-sectional view showing main parts of a distal end portion and a bending portion, and FIG. 13 is a cross-sectional view taken along XIII-XIII in FIG. 12.

Figure 1:
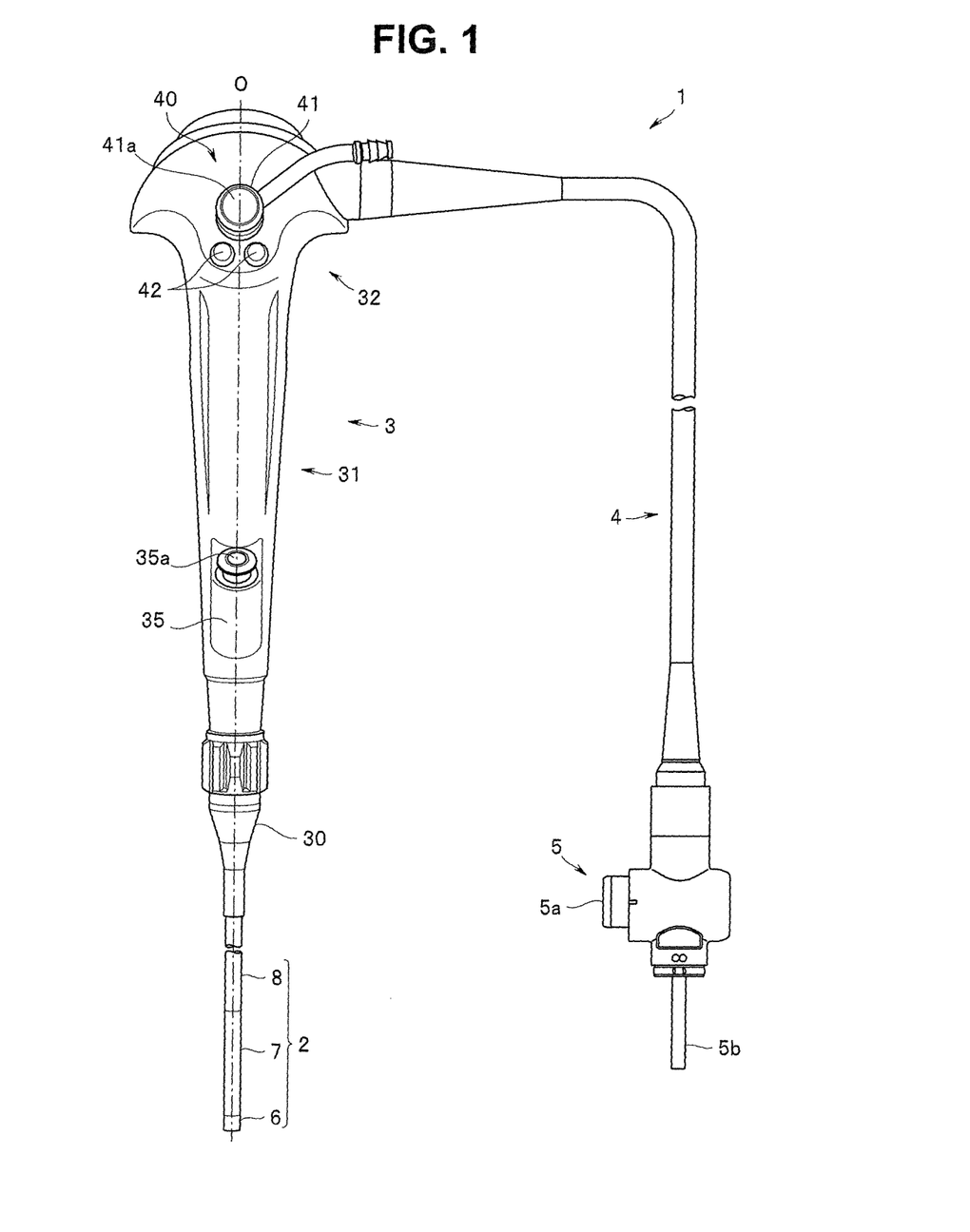
FIG. 1 is a front view showing an external appearance of an endoscope.
Figure 2:
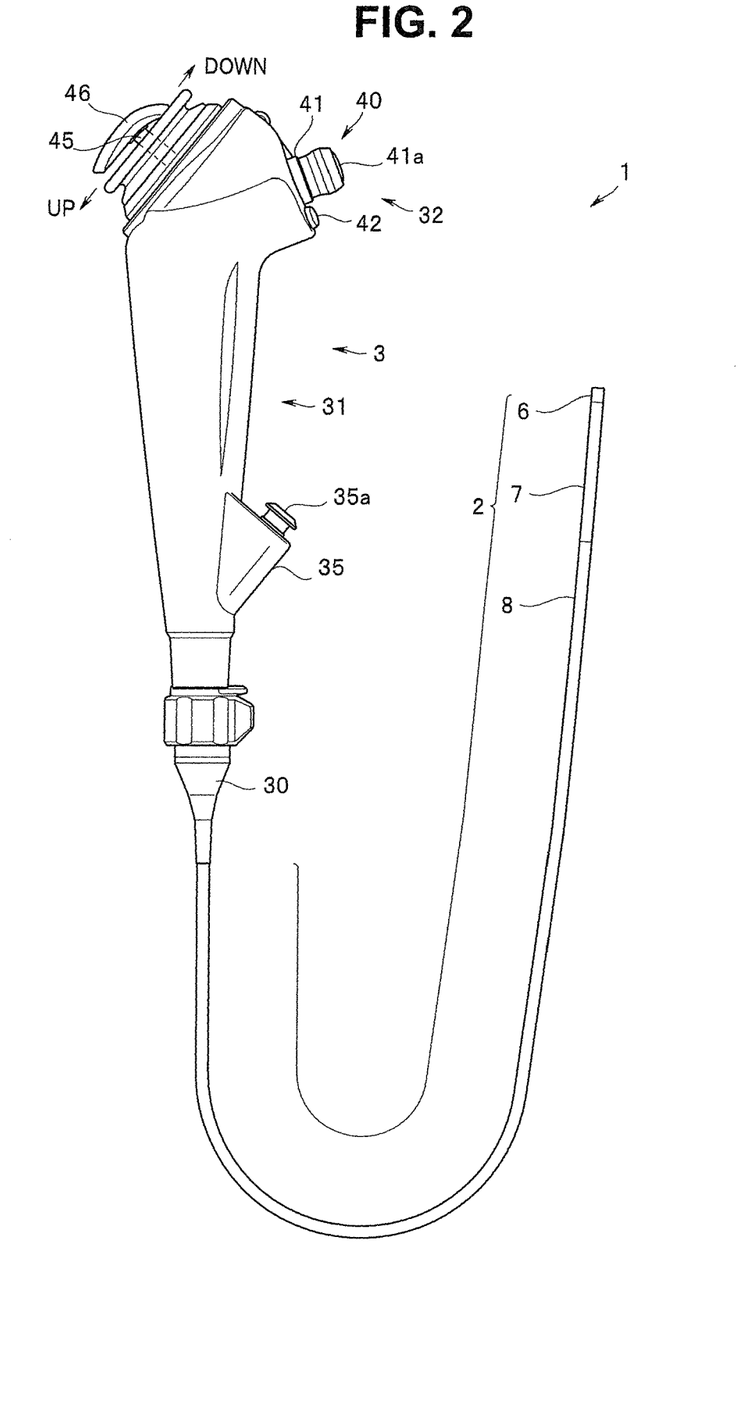
FIG. 2 is a right side view showing the external appearance of the endoscope.

As shown in FIGS. 1 and 2, an endoscope 1 of the present embodiment is a bronchus endoscope, and the endoscope 1 is configured by including an elongated tubular insertion section 2, an operation section 3 which is provided continuously to a proximal end of the insertion section 2, a universal cord 4 which is an endoscope cable extending from the operation section 3, and an endoscope connector 5 disposed at a distal end of the universal cord 4.

The insertion section 2 is configured by a flexible tubular member having a distal end portion 6, a bending portion 7, and a flexible tube portion 8 provided in a continuous manner from the distal end side.

Figure 12:
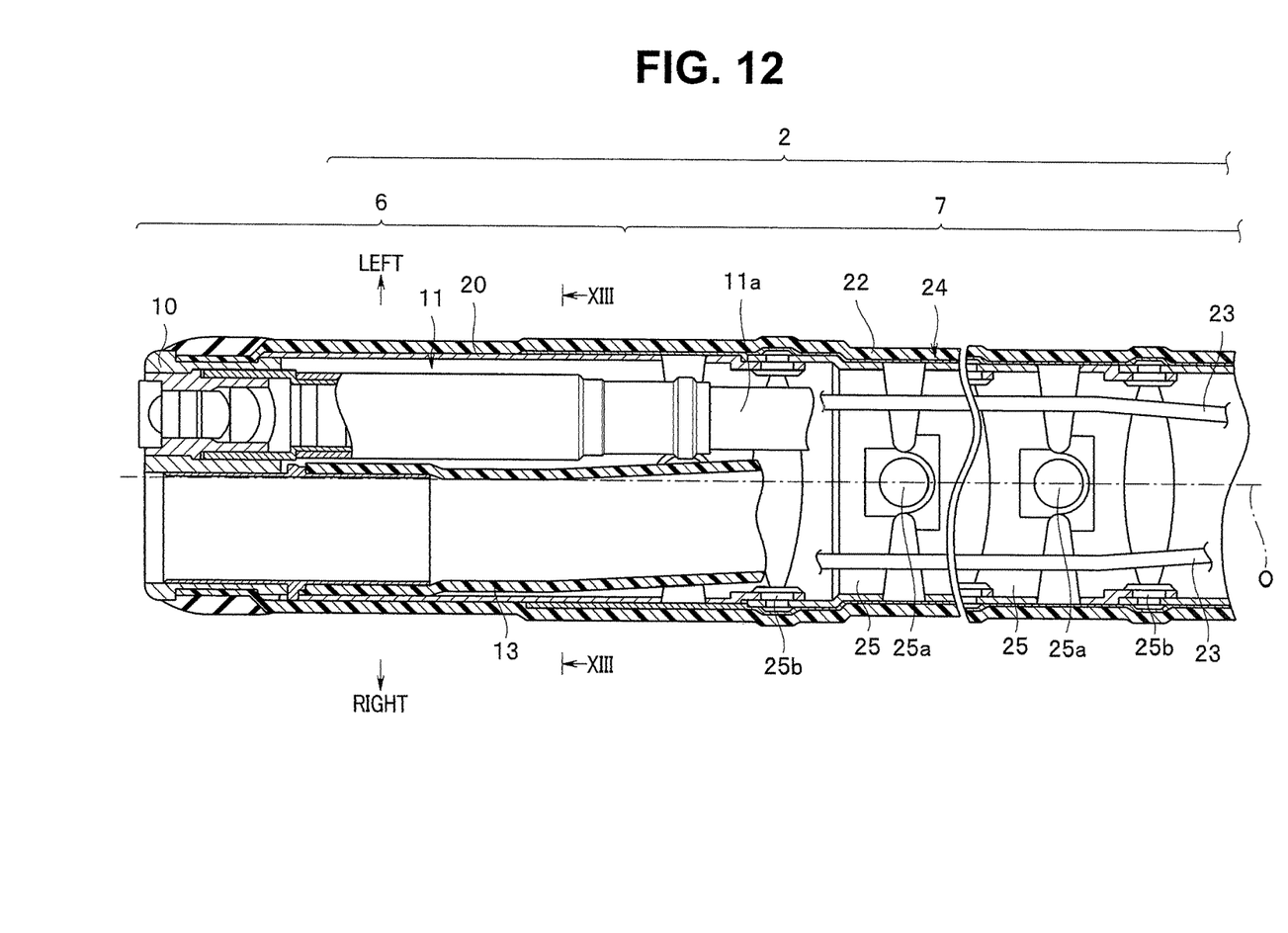
FIG. 12 is a transverse cross-sectional view showing main parts of a distal end portion and a bending portion.
Figure 13:
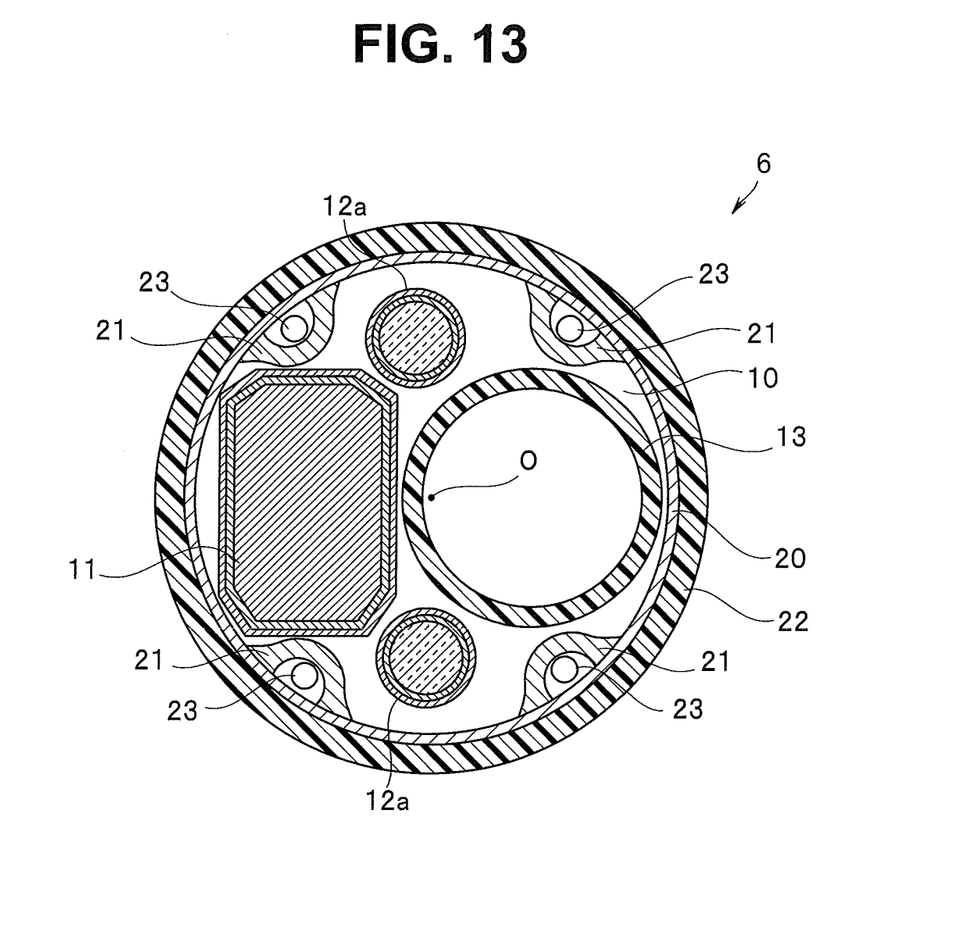
FIG. 13 is a cross-sectional view taken along XIII-XIII in FIG. 12.

For example, as shown in FIGS. 12 and 13, a metal distal end rigid portion 10 is provided inside the distal end portion 6, and an image pickup unit 11 where an image pickup device, such as a CCD or a CMOS, is built in, a pair of light guides 12a, and a treatment instrument insertion channel 13 are held in the distal end rigid portion 10.

Furthermore, inside the distal end portion 6, a most distal end bending piece 20 having the shape of a substantially circular cylinder is fitted on the proximal end side of the distal end rigid portion 10, and an outer circumference of the most distal end bending piece 20 is covered with bending rubber 22. Wire fixing portions 21 are provided on an inner circumference of the most distal end bending piece 20, at four positions around an insertion axis O, and respective distal ends of respective four angle wires (pull wires) 23 inserted in the insertion section 2 are fixed to the respective wire fixing portions 21.

To efficiently arrange each of the structural members without increasing the diameter of the distal end portion 6, the image pickup unit 11 and the treatment instrument insertion channel 13, which are large members, are arranged horizontally next to each other inside the distal end rigid portion 10 and the most distal end bending piece 20 (see FIG. 13), and the light guides 12a are arranged, respectively, in spaces at the top and the bottom formed by the arrangement mentioned above.

Furthermore, to prevent interference of the image pickup unit 11 and the treatment instrument insertion channel 13 with each angle wire 23, the respective wire fixing portions 21 are provided at positions rotated by predetermined angles, around the insertion axis O, from up/down/left/right positions of the distal end portion 6. That is, as shown in FIG. 13, the wire fixing portions 21 are provided to the most distal end bending piece 20, at positions rotated to the left/right from the up direction of the distal end portion 6, around the insertion axis O and in the range of 15 degrees to 75 degrees, and at positions rotated to the left/right from the down direction of the distal end portion 6, around the insertion axis O and in the range of 15 degrees to 75 degrees, for example.

The bending portion 7 is configured to be able to actively bend in any direction from the insertion axis O, including the up-down/right-left directions, according to an operation input from a surgeon or the like to the operation section 3. That is, the bending portion 7 of the present embodiment is configured by including a bending piece set 24 where a plurality of bending pieces 25 are coupled alternately by pivot portions 25a which are arranged in the up-down direction of the insertion section 2 and pivot portions 25b which are arranged in the right-left direction of the insertion section 2.

Inside the bending piece set 24, the signal cable 11a extending from the image pickup unit 11, the light guides 12a, and the treatment instrument insertion channel 13 are inserted according to an arrangement substantially the same as the arrangement inside the distal end portion 6. Furthermore, wire guides (not shown) through which respective angle wires 23 are inserted are formed to predetermined bending pieces 25 configuring the bending piece set 24, at substantially the same positions, around the insertion axis O, as the positions of the respective wire fixing portions 21 described above. Moreover, an outer circumference of the bending piece set 24 is covered with the bending rubber 22 extending from the distal end portion 6 side.

The flexible tube portion 8 is configured by a flexible tubular member which is capable of passively bending. The signal cable 11a, the light guides 12a, and the treatment instrument insertion channel 13 (which are not shown in the drawing) are inserted in the flexible tube portion 8. Note that, although not shown, the proximal end sides of the pair of light guides 12a are bundled into one light guide 12 inside the flexible tube portion 8.

The operation section 3 is configured by including a bending preventing portion 30 which is connected to the flexible tube portion 8 while covering the proximal end of the flexible tube portion 8, a grasping portion 31 which is provided continuously to the bending preventing portion 30 and which can be grasped by a hand of a user or the like, and an operation section main body 32 which is provided continuously to the proximal end side of the grasping portion 31. Note that, in the present embodiment, directions and the like from the insertion axis O of the operation section 3 are defined relative to the state where the grasping portion 31 is grasped by the user or the like, and more specifically, front/back/left/right directions (a front surface, a back surface, left and right side surfaces, etc.) relative to the user or the like grasping the grasping portion 31 are defined for the operation section 3.

As shown in FIG. 1, the grasping portion 31 is formed into a shape that is right-left symmetrical with respect to the insertion axis O (center axis), and can be grasped in the same manner by either of the left or the right hands of the user or the like.

Furthermore, a treatment instrument insertion portion 35 is provided on a front surface on the distal end side of the grasping portion 31. The treatment instrument insertion portion 35 is configured by including a treatment instrument insertion opening 35a through which various treatment instruments (not shown) are inserted. Inside the operation section 3, the treatment instrument insertion opening 35a communicates with the treatment instrument insertion channel 13 via a branching member 36 (see FIGS. 10 and 11). Also, a forceps plug (not shown) which is a lid member configured to block the treatment instrument insertion opening 35a is freely attachable/detachable to/from the treatment instrument insertion portion 35.

The operation section main body 32 is configured, at the proximal end side of the grasping portion 31, by a hollow member having a substantially partially spherical shape which is expanded mainly on the left and the right sides and the front side. An operation button group 40 used for realizing various functions of the endoscope 1 is provided on the front surface side of the operation section main body 32. On the other hand, a bending lever 45 as an operation lever used for performing bending operation of the bending portion 7 is disposed on the rear surface side of the operation section main body 32. Furthermore, the universal cord 4 extends from one side portion (for example, the left side portion) of the operation section main body 32.

The universal cord 4 is a composite cable inside which the signal cable 11a, the light guide 12 and the like extending from the distal end portion 6 side to the operation section 3 through the inside of the insertion section 2 and further extending from the operation section 3 are inserted.

The endoscope connector 5 is configured by including an electrical connector portion 5a to which a signal cable that connects to a video processor of an external appliance (not shown) is connected, and a light source connector portion 5b to which a light guide and an electrical cable that connect to a light source device, which is an external appliance, are connected.

Next, the configuration of each part of the operation section main body 32 will be described in greater detail.

As shown in FIG. 1, the operation button group 40 is configured by including a suction button 41a protruding from a suction valve 41 which is detachably mounted on the operation section main body 32, and two button switches 42 to which arbitrary functions may be assigned from among various functions regarding the endoscope 1, for example.

The suction button 41a and the button switches 42 are arranged in a right-left symmetrical manner on the front surface side of the operation section main body 32. That is, in the present embodiment, the suction button 41a is arranged at the center in the right-left width direction of the operation section main body 32 in a manner overlapping the insertion axis O. Also, the two button switches 42 are arranged at right-left symmetrical positions across the insertion axis O, on the distal end side than the suction button 41a.

For example, as shown in FIG. 4, a cylinder 43 which is provided continuously to the suction valve 41 is provided inside the operation section main body 32. The suction valve 41 can be detachably mounted on the cylinder 43, and the cylinder 43 is arranged at the center in the right-left width direction of the operation section main body 32 in a manner overlapping the insertion axis O in accordance with the arrangement of the suction button 41a.

For example, the bending lever 45 is configured by a joystick type lever which can be tilted in any direction including up-down/right-left directions. The bending lever 45 is arranged on the rear surface side of the operation section main body 32, at a position where the bending lever 45 becomes right-left symmetrical. That is, in the present embodiment, the bending lever 45 is arranged at the center in the right-left width direction of the operation section main body 32 in a manner overlapping the insertion axis O. For example, as shown in FIG. 3, with respect to the tilt direction of the bending lever 45, the right-left direction of tilt operation is defined to be the right-left width direction of the operation section 3, which is a direction orthogonal to the insertion axis O, and the up-down direction is defined to be the direction which is orthogonal to the right-left width direction.

More specifically, the tilt directions of the bending lever 45 of the present embodiment are defined, for example, with the left side as viewed in FIG. 3 as the tilt direction for bending the bending portion 7 to the left (left tilt direction), the right side as viewed in FIG. 3 as the tilt direction for bending the bending portion 7 to the right (right tilt direction), the bottom side as viewed in FIG. 3 as the tilt direction for bending the bending portion 7 upward (upward tilt direction), and the top side as viewed in FIG. 3 as the tilt direction for bending the bending portion 7 downward (downward tilt direction).

At a tip portion of the bending lever 45, a finger rest portion 46 where a thumb or the like of a user or the like can come into contact is provided. Also, as shown in FIG. 8, inside the operation section 3, a wire pull mechanism 50 is provided continuously to the proximal end side of the bending lever 45, and moreover, each angle wire 23 is connected to the wire pull mechanism 50 via a relay lever mechanism 60. The bending lever 45 constitutes, together with the wire pull mechanism 50 and the relay lever mechanism 60, a bending operation device 70 configured to bend the bending portion 7 in an arbitrary direction.

As shown in FIGS. 5 to 8, the wire pull mechanism 50 is configured by including a housing 51, a rotating frame 52 which is rotatably (swingably) and pivotally supported inside the housing 51, a base member 53 which is rotatably (swingably) and pivotally supported inside the rotating frame 52, and a wire pull member 54 which is fixedly provided to the base member 53.

The housing 51 is formed from a member having a substantially circular cylindrical shape, and shaft holes 51a that face each other pierce a circumferential wall of the housing 51.

The rotating frame 52 is formed from a frame body having a substantially rectangular shape, for example. A pair of screw holes 52a that face each other pierce the rotating frame 52 at the center of both end portions in the long side direction, and a pair of shaft holes 52b that face each other pierce the rotating frame 52 at the center of both end portions in the short side direction. The rotating frame 52 is rotatably and pivotally supported by the housing 51 by screws 55 being inserted in the respective shaft holes 51a of the housing 51 and screwed into the respective screw holes 52a.

The base member 53 is formed from a member having a substantially columnar shape. The bending lever 45 is integrally formed with the base member 53, at the center axis. Also, a pair of flat portions 53b that face each other are formed to a circumferential portion of the base member 53, and screw holes 53c pierce in a manner penetrating the flat portions 53b. Screws 56 inserted through the respective shaft holes 52b of the rotating frame 52 are screwed into the screw holes 53c, and the base member 53 is thereby rotatably and pivotally supported by the rotating frame 52. Moreover, the base member 53 is supported by the housing 51 via the rotating frame 52, and the bending lever 45 which is provided integrally and continuously to the base member 53 is thereby enabled to tilt in an arbitrary direction.

The wire pull member 54 is formed from a plate member having arm portions 54b extending in four mutually different directions. More specifically, in the present embodiment, the wire pull member 54 is formed from a cross-shaped plate member where the angle formed by mutually adjacent arm portions 54b is 90 degrees, and a center portion 54a is fixed to the base member 53 by screws 57. That is, the bending lever 45 is coupled to the wire pull member 54 by the base member 53, and the distal end side of each arm portion 54b is enabled to be displaced according to tilting motion of the bending lever 45. Furthermore, a wire fixing hole 54c pierces the distal end side of respective arm portions 54b which are supported in a displaceable manner as described above. Note that the angle formed by the respective arm portions 54b is not limited to 90 degrees, and may be arbitrarily changed in the range of ±30 degrees from 90 degrees, for example.

The wire pull mechanism 50 configured in the above manner is arranged inside the operation section main body 32 where the wire pull mechanism 50 and the cylinder 43 face each other with one behind the other. Here, the wire pull mechanism 50 is arranged with each arm portion 54b at a position rotated around a center axis O1 of the bending lever 45 in a range of 30 degrees to 60 degrees (for example, at a position rotated by 45 degrees) relative to the upward/downward/left/right tilt direction defined for the bending lever 45. For example, as shown in FIG. 4, the wire pull mechanism 50 is arranged with the cylinder 43 positioned between two arm portions 54b of the wire pull member 54.

The proximal end side of a suction pipeline 37 serving as a pipeline section is connected to the cylinder 43, and the distal end side of the suction pipeline 37 communicates with the treatment instrument insertion channel 13 via the branching member 36.

As shown in FIGS. 8 and 9, the relay lever mechanism 60 is configured by including a pair of left and right stays 61a, 61b serving as support members extending from the inside of the operation section main body 32 to the inside of the grasping portion 31, and four relay levers 62 supported by the stays 61a, 61b.

For example, as shown in FIG. 7, the proximal end sides of the stays 61a, 61b are integrally coupled by a coupling portion 61c. A pair of screw holes 61d pierce the coupling portion 61c, and screws 64 inserted through the screw holes 61d are screwed into brackets 51b provided in a protruding manner from the housing 51. The proximal ends of the stays 61a, 61b are thereby held inside the operation section main body 32 via the housing 51. Moreover, as shown in FIGS. 7 to 11, in the present embodiment, the pair of stays 61a, 61b held inside the operation section main body 32 in the above manner extend into the grasping portion 31 along the direction of longitudinal axis O while facing each other.

As shown in FIG. 10, in the present embodiment, one of the pair of stays 61a, 61b, namely, the stay 61a, functions as a so-called "bottom board" which is disposed with the aim of securing rigidity of the operation section 3, for example. The stay 61a extends to the distal end of the grasping portion 31 along the longitudinal axis O, and supports, at the distal end portion, the branching member 36 by screwing and the proximal end of the insertion section 2 by riveting, for example. In other words, in the present embodiment, a bottom board provided to stiffen the operation section 3 is to serve also as the stay 61a.

Furthermore, the suction pipeline 37 described above is disposed between the stays 61a, 61b. That is, the suction pipeline 37 is disposed to extend in the direction of the longitudinal axis O along the stays 61a, 61b by having the proximal end side fixed to the operation section 3 (the operation section main body 32) via the cylinder 43 and the distal end side fixed to the operation section 3 (the grasping portion 31) via the branching member 36 held by the stay 61a. Moreover, the internal space of the operation section 3 is partitioned into a first space portion 3a and a second space portion 3b by the stays 61a, 61b and the suction pipeline 37 disposed next to one another.

Long internal components including the signal cable 11a and the light guide 12 are disposed in the second space portion 3b of the partitioned internal spaces. Note that, as shown in FIG. 4, the proximal end sides of long internal components inserted in the second space portion 3b, such as the signal cable 11a and the light guide 12, pass by the side of the cylinder 43 and extend into the universal cord 4, for example.

On the other hand, each angle wire 23 connected to the wire pull mechanism 50 via the relay lever mechanism 60 is disposed in the first space portion 3a.

As shown in FIGS. 8 to 11, the relay levers 62 constituting the relay lever mechanism 60 are arranged in one line in the right-left direction inside the grasping portion 31. Fixed end sides of the relay levers 62 are pivotally supported by a single shaft portion 63 installed between the left and the right stays 61a, 61b, and free end sides of the respective relay levers 62 are thereby enabled to swing inside the first space portion 3a.

Each relay lever 62 corresponds to the respective arm portion 54b of the wire pull mechanism 50, and a point of effort 62a to which the amount of displacement of each arm portion 54b according to the tilting motion of the bending lever 45 is transmitted through the relay wire 65 is set at a mid-point of the respective relay lever 62. Moreover, a point of load 62b for amplifying the amount of displacement of each arm portion 54b and transmitting the amount of displacement to the respective angle wire 23 is set at the free end side of each relay lever 62, at a position separated from a fulcrum (shaft portion 63) than the point of effort 62a.

More specifically, for example, as shown in FIGS. 8 and 9, the proximal end side of the relay wire 65 is connected to the wire fixing hole 54c of respective arm portion 54b. On the other hand, a screw-type first wire adjustment portion 66 configured to adjust the length of the relay wire 65 is provided at the point of effort 62a of each relay lever 62, and the distal end side of the relay wire 65 is connected via the first wire adjustment portion 66. Moreover, a pulley 68 which is supported by the operation section main body 32 is engaged at a mid-point of each relay wire 65.

Moreover, the proximal end side of each relay wire 65 is adjusted, according to the setting regarding the disposed position of the respective pulley 68 or the like, to be oriented at an angle within a predetermined angle range with respect to a vertical direction of the arm portion 54b when the bending lever 45 is in a neutral state (for example, such an angle is an angle within an error range of about ±20 degrees with respect to the vertical direction of the arm portion 54b). Furthermore, the distal end side of each relay wire 65 is adjusted, according to the setting regarding the disposed position of the respective pulley 68 or the like, to be oriented at an angle within a predetermined angle range with respect to a vertical direction of the relay lever 62 when the bending lever 45 is in the neutral state (for example, such an angle is an angle within an error range of about ±20 degrees with respect to the vertical direction of the relay lever 62).

Furthermore, for example, as shown in FIGS. 8 and 9, a screw-type second wire adjustment portion 67 configured to adjust the length of the angle wire 23 is provided to the point of load 62b of each relay lever 62, and the proximal end side of the angle wire 23 is connected to the point of load 62b via the second wire adjustment portion 67. Note that the respective angle wires 23 are routed inside the insertion section 2 with the distal end sides crossed between up and down and left and right.

According to such a configuration, for example, when a user or the like grasps the grasping portion 31 of the operation section 3 and tilts the bending lever 45 in the left tilt direction by the thumb of the grasping hand, the relay wires 65 coupled to the two arm portions 54b positioned in the right tilt direction are mainly pulled. The pull on the relay wires 65 is transmitted to the corresponding respective relay levers 62, and each relay lever 62 is caused to swing at an angle according to the amount of pull. Accordingly, inside the bending portion 7, the two angle wires 23 positioned on the left side in the bending direction are mainly pulled by the amount of pull amplified by the relay levers 62, and the bending portion 7 is bent to the left. At this time, each angle wire 23 moves forward/backward inside the operation section 3, but because each angle wire 23 is disposed inside the first space portion 3a and other long internal components, such as the signal cable 11a and the light guide 12, are disposed in the second space portion 3b partitioned off by the stays 61a, 61b and the suction pipeline 37, interference between each angle wire 23 and other long internal components is appropriately prevented.

Furthermore, for example, when a user or the like grasps the grasping portion 31 of the operation section 3 and tilts the bending lever 45 in the right tilt direction by the thumb of the grasping hand, the relay wires 65 coupled to the two arm portions 54b positioned in the left tilt direction are mainly pulled. The pull on the relay wires 65 is transmitted to the corresponding respective relay levers 62, and each relay lever 62 is caused to swing at an angle according to the amount of pull. Accordingly, inside the bending portion 7, the two angle wires 23 positioned on the right side in the bending direction are mainly pulled by the amount of pull amplified by the relay levers 62, and the bending portion 7 is bent to the right. At this time, each angle wire 23 moves forward/backward inside the operation section 3, but because each angle wire 23 is disposed inside the first space portion 3a and other long internal components, such as the signal cable 11a and the light guide 12, are disposed in the second space portion 3b partitioned off by the stays 61a, 61b and the suction pipeline 37, interference between each angle wire 23 and other long internal components is appropriately prevented.

Furthermore, for example, when a user or the like grasps the grasping portion 31 of the operation section 3 and tilts the bending lever 45 in the upward tilt direction by the thumb of the grasping hand, the relay wires 65 coupled to the two arm portions 54b positioned in the downward tilt direction are mainly pulled. The pull on the relay wires 65 is transmitted to the corresponding respective relay levers 62, and each relay lever 62 is caused to swing at an angle according to the amount of pull. Accordingly, inside the bending portion 7, the two angle wires 23 positioned on the bottom side in the bending direction are mainly pulled by the amount of pull amplified by the relay levers 62, and the bending portion 7 is bent upward. At this time, each angle wire 23 moves forward/backward inside the operation section 3, but because each angle wire 23 is disposed inside the first space portion 3a and other long internal components, such as the signal cable 11a and the light guide 12, are disposed in the second space portion 3b partitioned off by the stays 61a, 61b and the suction pipeline 37, interference between each angle wire 23 and other long internal components is appropriately prevented.

Furthermore, for example, when a user or the like grasps the grasping portion 31 of the operation section 3 and tilts the bending lever 45 in the downward tilt direction by the thumb of the grasping hand, the relay wires 65 coupled to the two arm portions 54b positioned in the upward tilt direction are mainly pulled. The pull on the relay wires 65 is transmitted to the corresponding respective relay levers 62, and each relay lever 62 is caused to swing at an angle according to the amount of pull. Accordingly, inside the bending portion 7, the two angle wires 23 positioned on the top side in the bending direction are mainly pulled by the amount of pull amplified by the relay levers 62, and the bending portion 7 is bent downward. At this time, each angle wire 23 moves forward/backward inside the operation section 3, but because each angle wire 23 is disposed inside the first space portion 3a and other long internal components, such as the signal cable 11a and the light guide 12, are disposed in the second space portion 3b partitioned off by the stays 61a, 61b and the suction pipeline 37, interference between each angle wire 23 and other long internal components is appropriately prevented.

According to such an embodiment, the grasping portion 31 may be efficiently miniaturized while preventing interference between the angle wires 23 and other internal components, by partitioning the inside of the operation section 3 into the first space portion 3a and the second space portion 3b by using the stays 61a, 61b which extend inside the operation section 3 along the direction of the longitudinal axis O and the suction pipeline 37 which extends inside the operation section 3 in the direction of the longitudinal axis O and along the stays 61a, 61b and the distal end side and the proximal end side of which are fixed to the operation section 3, by disposing each angle wire 23 inside the first space portion 3a, and by disposing long internal components, such as the signal cable 11a and the light guide 12, inside the second space portion 3b.

That is, by arranging the stays 61a, 61b which function as support members and the suction pipeline 37 which functions as a predetermined pipeline section next to one another and partitioning the inside of the operation section 3 into the first space portion 3a and the second space portion 3b, each angle wire 23 and long internal components, such as the signal cable 11a and the light guide 12, may be disposed in separate spaces (the first and the second space portions 3a, 3b) without using a dedicated partition or the like. Moreover, by disposing each angle wire 23 and other long components in the separate first and second space portions 3a, 3b, the internal space of the operation section 3 does not have to be made larger than necessary for the purpose of preventing interference, and the grasping portion 31 can be efficiently miniaturized (by reducing the diameter, for example).

In this case, by interposing the relay lever 62 between the wire pull mechanism 50 and the respective angle wires 23, the extending direction of the respective angle wires 23 can be easily adjusted at the time of arranging the respective angle wires 23 inside the first space portion 3a.

Particularly, by arranging and pivotally supporting the respective relay levers 62 on the single shaft portion 63, the relay levers 62 may be arranged at one position, and the respective angle wires 23 may be arranged while being efficiently aligned inside the first space portion 3a.

Furthermore, the stay 61a supporting each relay lever 62 serves also as a so-called bottom board, and thus, even in a case where the relay levers 62 are provided, an unnecessary increase in the number of components may be suppressed, and the grasping portion 31 may be efficiently miniaturized.

Note that the present invention is not limited to each embodiment described above, and various modifications and changes may be made within the technical scope of the present invention.

For example, the long internal components are not limited to the signal cable 11a and the light guide 12 mentioned above, and may include various other internal components according to the type of the endoscope.

Furthermore, the embodiment described above describes an example of a configuration where a pair of stays 61a, 61b are provided inside the operation section 3 as support members, but the present invention is not limited to such a case, and the stay 61b may be omitted as appropriate, for example. In contrast, the pair of stays 61a, 61b may both be extended to the distal end of the grasping portion 31 to serve also as the so-called bottom boards, with the aim of further increasing the rigidity of the operation section 3.

What is claimed is:

1. An endoscope comprising:
an insertion section configured to be inserted into a subject, and bendable in at least two directions with a longitudinal axis direction as a center;
an operation section disposed on a proximal end side of the insertion section;
a support member extending from a distal end side to a proximal end side of the operation section inside the operation section, along the longitudinal axis direction;
a pipeline section fixed to the operation section at a distal end side and a proximal end side so as to extend inside the operation section, along the support member and in the longitudinal axis direction, and disposed next to the support member to partition, with the support member, an internal space of the operation section into a first space portion and a second space portion;

an angle wire disposed in the first space portion inside the operation section, and configured to cause the bending portion to bend; and a long internal component disposed in the second space portion inside the operation section, and extending from the insertion section;

wherein a relay lever is interposed between a wire pull mechanism configured to pull the angle wire and the angle wire;

wherein the relay lever includes a fulcrum supported by the support member, a point of effort that is set at a mid-point of the relay lever and is connected to the wire pull mechanism via a relay wire, and a point of load that is set at a free end side of the relay lever separated from the fulcrum than the point of effort and is connected to the angle wire.

2. The endoscope according to claim 1, wherein the pipeline section is a suction pipeline that communicates, inside the operation section, with a treatment instrument insertion channel inserted in the insertion section.

\* \* \* \* \*